(12) United States Patent
Kondo et al.

(10) Patent No.: US 7,157,093 B1
(45) Date of Patent: *Jan. 2, 2007

(54) OIL CLEANING SHEETS FOR MAKEUP

(75) Inventors: Kazunori Kondo, Sagamihara (JP); Kumiko Etchu, Sagamihara (JP)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/582,838

(22) PCT Filed: Dec. 4, 1998

(86) PCT No.: PCT/US98/25736

§ 371 (c)(1), (2), (4) Date: Jan. 4, 2001

(87) PCT Pub. No.: WO99/29220

PCT Pub. Date: Jun. 17, 1999

(30) Foreign Application Priority Data

Dec. 5, 1997 (JP) .................................. 9-335451
Dec. 3, 1998 (JP) ................................. 10-343839

(51) Int. Cl.
*A61K 6/00* (2006.01)
*A61K 9/00* (2006.01)
*A01N 25/34* (2006.01)

(52) U.S. Cl. ...................... 424/401; 424/400; 424/402

(58) Field of Classification Search ................ 424/400, 424/401, 402; 604/379; 206/494; 428/311.11
See application file for complete search history.

(56) References Cited

U.S. PATENT DOCUMENTS

| | | | |
|---|---|---|---|
| 1,205,892 A | 11/1916 | Hecht | |
| 2,032,150 A | 2/1936 | Richardson | |
| 2,269,525 A | 1/1942 | Fleischer | |
| 2,341,794 A | 2/1944 | Kliwer | |
| 2,885,112 A | 5/1959 | Willat | |
| 3,825,379 A | 7/1974 | Lohkamp et al. | |
| 3,971,373 A | 7/1976 | Braun | |
| 4,279,890 A | 7/1981 | Harris et al. | |
| 4,532,937 A * | 8/1985 | Miller | 600/572 |
| 4,574,952 A | 3/1986 | Masui | |
| 4,587,154 A | 5/1986 | Hotchkiss et al. | |
| 4,643,939 A | 2/1987 | Sugiyama et al. | |
| 4,726,989 A | 2/1988 | Mrozinski | |
| 4,739,902 A | 4/1988 | Joslyn et al. | |
| 4,755,178 A | 7/1988 | Insley et al. | |
| 4,818,463 A | 4/1989 | Buehning | |
| 4,822,350 A * | 4/1989 | Ito et al. | 604/372 |
| 4,907,174 A | 3/1990 | Priem | |
| 4,986,743 A | 1/1991 | Buehning | |
| 5,046,640 A | 9/1991 | Carroll | |
| 5,119,828 A | 6/1992 | Miller | |
| 5,144,744 A | 9/1992 | Campagnoli | |
| 5,184,725 A | 2/1993 | Reinheimer et al. | |
| 5,744,149 A | 4/1998 | Girardot | |
| 5,935,521 A | 8/1999 | Khazaka | |
| 6,042,844 A * | 3/2000 | Ishida et al. | 424/443 |
| 6,214,362 B1 | 4/2001 | Page | |
| 6,533,119 B1 * | 3/2003 | Hansen et al. | 206/494 |
| 6,638,611 B1 * | 10/2003 | Seth | 428/304.4 |
| 6,645,611 B1 * | 11/2003 | Seth | 428/311.11 |
| 6,773,718 B1 * | 8/2004 | Seth et al. | 424/443 |

FOREIGN PATENT DOCUMENTS

| | | |
|---|---|---|
| DE | 4209025 | 3/1992 |
| EP | 0 821 153 B1 | 1/1998 |
| EP | 1066826 | 1/2001 |
| GB | 2061709 | 5/1981 |
| JP | 56-008606 | 1/1981 |
| JP | 58-74894 | 5/1983 |
| JP | 04-045591 | 2/1992 |
| JP | 5018392 | 1/1993 |
| JP | 6-25277 | 4/1994 |
| JP | H06-25277 | 4/1994 |
| JP | 6319664 | 11/1994 |
| JP | 10-15304 | 1/1998 |
| JP | H10-15304 | 1/1998 |
| WO | WO 99/29220 | 6/1999 |
| WO | WO 01/85001 | 11/2001 |

OTHER PUBLICATIONS

Wente Van A., "Superfine Thermoplastic Fibers", *Industrial Engineering Chemistry*, vol. 48, p. 1342 et seq. (1956).
Wente et al., "Manufacture of Superfine Organic Fibers", Report No. 4364 of the Naval Research Laboratories, published May 25, 1954.
U.S. Appl. No. 09/566,308.
U.S. Appl. No. 09/585,649.
U.S. Appl. No. 09/780,094.

* cited by examiner

*Primary Examiner*—Michael P. Woodward
*Assistant Examiner*—Lakshmi Channavajjala
(74) *Attorney, Agent, or Firm*—William J. Bond

(57) ABSTRACT

To provide an oil cleaning sheet for makeup which has excellent oil absorption, allows clear assessment of the oil absorbing effect by becoming transparent upon oil absorption, thus providing the user with a feeling of adequate wiping and a sense of satisfaction, has an agreeable feel, is resistant to damage during use and which does not require inclusion of particulate bodies on the surface. The oil cleaning sheet consists of a porous stretched film made of a plastic material.

8 Claims, No Drawings

OIL CLEANING SHEETS FOR MAKEUP

FIELD OF THE INVENTION

The present invention relates to an oil cleaning sheet for makeup, and more specifically it relates to an oil cleaning sheet in the form of strip for wiping off skin oil (sebum) which has surfaced on the face. The oil cleaning sheet of the invention has excellent oil absorbance, allows the condition of oil to be easily assessed when applying makeup and causes little skin irritation, while its facial cleansing effect is excellent, thus facilitating application and spreading of cosmetics.

In addition to excellent absorption of the skin oil, notable transparency which is effective to know a level of the oil absorption and toughness, the oil cleaning sheet of the invention can absorb a large amount of sweat and skin oil dissolved therein on the face, because a surface of the sheet has a good hydrophilic property.

BACKGROUND

Various types of oil cleaning sheets for makeup are well known, for wiping off oils which surface on different parts of the face, especially the nose, cheeks, forehead and eyebrows, to maintain a clean face and to facilitate application and spreading of cosmetics. When makeup is applied over oils which have surfaced on the face, the cosmetic material fails to properly adhere to the skin, thus impeding its spreading and preventing adequate performance of the effect of the makeup. An additional effect can be exhibited after makeup is applied, to prevent crumbling of the makeup or "oily appearance", by using oil cleaning sheets to wipe off oils which constantly surface on the skin after application of makeup.

The most widely used type of oil cleaning sheets among the many kinds of oil cleaning sheets are those obtained by making paper from oil absorbing plant fibers such as hemp or synthetic pulp. Sheets made from these paper materials, however, while having high oil absorption, also have a disadvantage of high irritation to skin as a result of the hardness and surface roughness of the fiber materials used. In order to overcome this irritation to the skin, high-compression roller pressing is carried out during production of the oil cleaning sheets, or the surface of the paper may be coated with an inorganic powder such as calcium carbonate powder along with a sizing agent. However, in the former case there is again the disadvantage of skin irritation, because the fibers smashed by the roll pressing become raised over time, while in the latter case a disadvantage results in that the surface of the paper becomes covered with the sizing agent, unavoidably lowering the oil absorbing power.

Japanese Unexamined Utility Model Publication (Kokai) No. 4-45591 is aimed particularly at solving the problems caused by roll pressing during production of oil cleaning sheets and by coating of paper surfaces with inorganic powders such as calcium carbonate powder, and it teaches adhesion of porous globular beads onto the surface of oil cleaning sheets. According to this proposal, adhesion of porous globular beads onto the surface of oil cleaning sheets. According to this proposal, adhesion of porous globular beads provides an effect of allowing efficient absorption of skin oils.

Also, Japanese Unexamined Patent Publication (Kokai) No. 6-319664 teaches improvement in skin oil absorption by adding (B) an inorganic filler to (A) a raw pulp material composed mainly of plant fiber for preparation of a paper making material, to make sheets with a paper hardness of at least 0.7 (g/cm$^2$).

The oil cleaning sheets produced by the methods taught in these publications are effective at reducing irritation to skin during their use. However, the improvement in skin oil absorption with these oil cleaning sheets is limited, and further improvement is therefore desired. These oil cleaning sheets also have an additional problem in that the state of oil absorption of skin oils, i.e. the wiping effect cannot be easily and accurately assessed during their use. The difficulty in assessing the wiping effect means that the user cannot achieve satisfaction by the removal of skin oils from the face. That is, from the point of view of the user, it is a very important evaluating factor to determine whether and how much skin oils have been removed from the face of the user when the oil cleaning sheets are used, and therefore satisfaction with makeup application varies greatly depending on this factor.

There also exist publicly known oil cleaning sheets for makeup which especially focus on allowing easy assessment of the wiping effect on skin oils, as discussed above. For example, Japanese Examined Patent Publication No. 56-8606 teaches an oil cleaning sheet for makeup which is characterized by mixture of hemp fibers with polyolefin resin fibers in an amount of 10–70% by weight and preparation of sheets with a density of 12–50 g/cm$^2$. Because these oil cleaning sheets have a construction with transparent-like polyolefin fibers mixed with non-transparent hemp fibers, the hemp fibers which are non-transparent prior to use exhibit a transparent-like property upon absorption of oil, thus allowing the skin oil wiping effect to be clearly assessed.

In addition, Japanese Unexamined Utility Model Publication (Kokai) No, 5-18392 discloses oil cleaning sheets characterized in that inorganic or organic particulate bodies such as clay particles, fine silica particles, fiber powder or the like are added to oil cleaning paper to form a smooth side on the surface of the oil cleaning paper. Since these oil cleaning sheets contain particles in the gaps between the fibers of the oil cleaning paper, skin oils moisturize the entirety of the oil cleaning sheet while also filling the gaps between the paper fibers and the particles, providing an effect of rendering the oil cleaning paper even more transparent, i.e, giving the user a "satisfaction that skin oil has been removed".

Nevertheless, although the 2 types of oil cleaning sheets mentioned above exhibit certain degrees of effects of transparency by oil absorption and assessment of oil absorption thereby, as a drawback they have a reduced amount of oil absorption which is the most important aspect for oil cleaning sheets, and it is difficult to achieve full transparency of the oil cleaning sheets upon oil absorption. Consequently, there still remains a demand for oil cleaning sheets with even greater oil absorption which can also be rendered transparent to give adequate satisfaction to users.

Another problem which is common to conventional oil cleaning sheets arises from the fact that they are made from paper types produced as thin paper from fiber materials, and thus they tend to be easily damaged when the user employs them to wipe skin oils from the face and must be immediately replaced. Because of the high cost of commercially available oil cleaning sheets, it is desireable to provide tougher oil cleaning sheets which do not need such immediate replacement.

In addition to the above problems, the prior art oil cleaning sheets suffer from another problem in the summer season and in an air-conditioned room under the highly increased temperature, because under such conditions, the oil cleaning sheets are insufficient to completely remove the sweat from the face surface. The unremoved sweat further causes insufficient compatibility and adhesion of the cosmetic material to the skin, because the sweat contains skin oil dissolved therein. It is therefore desired to provide an oil cleaning sheet having an excellent absorption capacity of liquid including sweat, in addition to excellent oil absorption capacity and other advantages.

DETAILED DESCRIPTION OF THE INVENTION

The present invention has been accomplished in the light of the many problems with conventional oil cleaning sheets for makeup which have been discussed above, and its object is that of providing an improved oil cleaning sheet for makeup which has excellent oil absorption, is resistant to damage during use, allows clear assessment of the oil absorbing effect by becoming transparent upon oil absorption to thus provide the user with a feeling of adequate wiping and a sense of satisfaction, has an agreeable feel, and which does not require inclusion of particulate bodies on the surface for improved characteristics.

Another object of the present invention is to provide an improved oil cleaning sheet for makeup which enables to absorb a large amount of sweat on the face and skin oil and the like dissolved in the sweat, in addition to ensuring excellent absorption of the skin oil, notable transparency capable of indicating a level of the oil absorption and toughness.

According to the present invention, the above-mentioned object may be achieved by an oil cleaning sheet for makeup characterized by comprising a porous stretched film made of a plastic material.

The porosity of the interstitial volume per unit area stretched film made of a plastic material as a constituent of the oil cleaning sheet for makeup according to the invention is preferably in the range of 0.0001–0.005 cm$^3$ as calculated by the equation:

Interstitial volume per unit area=[film thickness (cm)×1 (cm)×1 (cm)×void content (%)]/100 (where the void content is the percentage of voids in the porous film).

The "void content" is more specifically defined as the percentage of an amount of filling material, when all of the voids of the porous film are filled with a material of the same composition as the film, with respect to a film with no corresponding voids.

The void content of the porous stretched film is preferably in the range of 5–50% and the film thickness is preferably in the range of 5–200 μm.

Further, in the oil cleaning sheet of the present invention, it is preferred that at least one surface of the porous stretched film contains a hydrophilic liquid-absorbing substance which is at least partly distributed on the surface.

The distribution of the liquid-absorbing substance on the film surface can be provided in any desired step during production of the stretched film. Preferably, the liquid-absorbing substance is distributed on the surface of the stretched film by coating the same, after production of the film. Alternatively, the liquid-absorbing substance is preferably incorporated into the stretched film during production thereof, so that said substance is at least partly exposed in a surface of the film, thereby ensuring the desired functions and effects. The liquid-absorbing substance may be incorporated into a raw material or mixture of the film or an intermediate product of the film, for example.

In the above-described stretched film having the distributed liquid-absorbing substance, it is preferred that the stretched film has a liquid absorption capacity, in terms of the amount of water absorbed, of 0.00003 to 0.005 cm$^3$ per unit area. It is also preferred that an aqueous solution of the liquid-absorbing substance distributed on a surface of the stretched film has a surface tension of 15.0 to 36.0 dyn/cm.

The oil cleaning sheet for makeup according to the invention is characterized by employing as the paper body a plastic material as opposed to paper material such as used in conventional oil cleaning sheets, and preparing a porous stretched film with that material. The porous stretched film of the invention may be produced by various different methods using the plastic material as the starting substance, but preferably it is produced by various different methods using the plastic material as the starting substance, but preferably it is produced by adding a filler to a highly transparent crystalline thermoplastic resin as the starting material for film making to prepare a plastic film, and then stretching the film to crate fine voids therein.

The porous stretched plastic film obtained in this manner has a larger percentage of voids constituting the volume of the sheet compared to conventional oil cleaning sheets, and therefore it has excellent absorption of skin oils on the skin absorption per unit area. Also, since the plastic film has a structure with a uniform content of many fine voids, prior to wiping of skin oils from the skin surface it appears non-transparent due to light dispersion, but after oil absorption the oils fill each of the voids thus either preventing or reducing the degree of light dispersion, and this together with the original transparent nature of the film body allows the oil absorbing effect to be clearly assessed.

Preferred examples of highly transparent crystalline thermoplastic resins to be used as the main starting material for production of the porous unstretched plastic film of the invention include, but are not limited to, high density polyethylene, polypropylene, polybutylene, poly-4-methyl-pentene and ethylene-propylene block copolymer, while modified polypropylene is ideal because of its melt strength for film making.

Preferred examples of fillers to be used in combination with the aforementioned thermoplastic resin to provide the fine voids include, but are not limited to, mineral oils, glycerin, petroleum jelly, low molecular weight polyethylene, polyethylene oxide, polypropylene oxide, polytetramethylene oxide, soft Carbowax and mixtures thereof, because these exhibit transparency upon absorption of oil. Mineral oils are preferred among these fillers because of their relatively low cost.

The aforementioned fillers can be varied within a wide range in the starting material used for production of the film. The amount of filler to be used is preferably in the range of 20–60% by weight, and more preferably 25–40% by weight of the starting material. If the amount of filler added to the starting material is under 20% by weight, the void content of the film resulting after stretching is reduced, thus lowering the amount of oil absorption, while if it is above 60% by weight it becomes more difficult to produce films, and only brittle films can be obtained.

Other additives may also be added as necessary in addition to the thermoplastic resin and filler in the main starting material for production of the porous stretched plastic film. For example, organic acids such as carboxylic acid, sulfonic acid and phosphonic acid, and organic alcohols. As additional suitable additives there may be mentioned, for example, inorganic and organic pigment, aromatic agents, surfactants, antitstatic agents and the like.

The main starting material and optional additives are melted and combined to form a film, producing a filler-containing plastic film. The melting and mixing step and the subsequent film forming step may be carried out according to common methods. An example of a suitable melt mixing method is kneading with a kneader, and examples of suitable film forming methods are the inflation method and the casting method. The inflation method, for example, can give tube-shaped films by melt mixing the main starting material, etc. and then blowing it up from a circular die. The casting method can give films by melt mixing the main starting material, etc. and then extruding it from a die on a chilled roll (cold roll). In a modified form of this casting method, the additives may be removed by washing off with a suitable solvent after extrusion of the melted mixture on the chilled roll.

The formed plastic film is then stretched to provide it with fine voids. As with the film forming, the stretching may also be carried out according to common methods, such as uniaxial stretching or biaxial stretching. For example, in the case of biaxial stretching, the stretching in the lengthwise direction may be accomplished by varying the speed of the driving roll, and the stretching in the widthwise direction may be accomplished by mechanical pulling in the widthwise direction while holding both ends of the film with a chuck.

The conditions for the film stretching are not particularly restricted, but the stretching is preferably carried out so as to give a void content in the range of 5–50% and a stretched film thickness in the range of 5–200 μm. If the void content upon stretching of the film is under 5% the amount of oil absorption will be reduced, while if it is over 50% the amount of oil absorption will be too great, making it difficult to clearly assess the oil absorbing effect. Also, if the film thickness is under 5 μm the amount of oil absorption will be too low and the film will tend to adhere to areas of the face which require no removal of oils, making it more difficult to handle, while if it is over 200 μm the amount of oil absorption will be too great.

The stretching ratio for the plastic film is usually preferred to be in the range of 1.5 to 3.0. If the stretching ratio is under 1.5 it becomes impossible to achieve a sufficient void content for oil absorption, while if it is over 3.0 the void content becomes too large, causing too much oil absorption.

The size of the voids formed by stretching of the film is usually preferred to be in the range of 0.2 to 5 μm. If the void size is under 0.2 μm it becomes impossible to absorb enough skin oil to create transparency, while if it is over 5 μm the amount of oil absorption will be too great.

As mentioned above, the interstitial volume per unit area of the porous stretched plastic film obtained by the stretching process described earlier is preferably in the range of 0.0001–0.005 $cm^3$, and more preferably in the range of 0.0002–0.001 $cm^3$, as calculated by the equation defined above. If the interstitial volume of the film is under 0.0001 $cm^3$ it becomes difficult for the user to hold the oil cleaning sheet, while if it is over 0.005 $cm^3$ the amount of oil absorption is too great, and it becomes difficult to clearly assess the oil absorbing effect.

As described above, the oil cleaning sheet for makeup of the present invention can provide many advantages such as excellent absorption of skin oil, notable transparency enabling easy confirmation of oil absorption and toughness. However, since it is made of a plastic material, if it is compared with the prior art oil cleaning sheet made of paper, the present oil cleaning sheet suffers from the difficulty in effectively absorb the water-based liquid such as sweat. As a result of zealous examination, the inventors have found that a poor sweat absorption is principally due to a hydrophobic surface of the plastic film and accordingly if a hydrophilic property is given to the plastic film, it becomes to easily absorb the sweat on the face and the skin oil dissolved in the sweat.

That is, according to one preferred embodiment of the present invention, there is provided an oil cleaning sheet for makeup having an excellent hydrophilic property in which at least one surface of said porous stretched film contains a hydrophilic liquid-absorbing substance which is at least partly distributed on the surface.

The distribution of the hydrophilic liquid-absorbing substance in the hydrophilic oil cleaning sheet of the present invention is generally in such a state that fine particles of the liquid-absorbing substance is substantially uniformly dispersed in a surface of the porous stretched film. Further, since many different methods may be used to apply the liquid-absorbing substance to the film surface, if necessary, the liquid-absorbing substance may be also contained in the film. Furthermore, the liquid-absorbing substance may be distributed only on a single surface of the stretched film, if the oil cleaning sheet is designed to utilize such a single surface, or, alternatively, the substance may be distributed on both surfaces of the stretched film.

The application of the liquid-absorbing substance to the stretch film can be carried out by using different methods. For example, after production of the stretched film, the liquid-absorbing substance can be advantageously applied to a surface of the film by using a coating method. According to this coating method, for example, after the liquid-absorbing substance is dissolved in a suitable solvent, the resulting coating solution can be coated at a thinner thickness on a single or both surfaces of the stretched film, followed by drying the coating to remove the solvent therefrom, to thereby obtain the desired hydrophilic oil cleaning sheet.

The hydrophilic liquid-absorbing substance which can be advantageously used in the practice of the present invention, although it is not restricted to the specific one insorfar as it can provide the expected functions and effects, is preferably a surface active agent. This is because, for the present invention, when the liquid (liquid droplets) such as sweat on the face is wiped with the oil cleaning sheet, it is necessary to reduce a surface tension of the liquid droplets as a function of the inclusion of the liquid-absorbing substance in the liquid droplets, and to satisfy the above requirement, the presence of a substance capable of showing a high surface activity at a low concentration, i.e., suface active agent, is effective. Note in this connection that, as described above, a wide variety of additives may be added to starting material during production of the plastic film and typical examples thereof include a surface active agent, however, for this instance, the surface active agent is not used to give an excellent hydrophilic property to the film surface, but, to assist in good dispersion of the starting materials in the kneedering step.

The surface active agent suitable as the hydrophilic liquid-absorbing substance, although it is not restricted to, includes, for example:

Anionic surface active agent:

esters of alkylsulfuric acid, alkylbenzenesulfonates, esters of polyoxyethylene alkylphosphoric acid, and the like;

nonionic surface active agent 9:
polyoxyethylene alkylethers, esters of sorbitan aliphatic acid, and the like;
cationic surface active agent;
alkylamine salts,
quarternary ammonium salts, and the like; and
hydrophilic polymer;
polyvinyl alcohol, polyethylene glycol, polypropylene glycol and the like.

Among the above-described surface active agents, esters of sorbitan aliphatic acid, typically sorbitan monolaurate can be particularly advantageously used, because they have good capability of providing a hydrophilic property in the film surface, along with a safety to the skin.

When the hydrophilic liquid-absorbing substance is used to prepare a coating solution, suitable solvents, although they are not restricted to, include, for example, isopropyl alcohol, ethanol, water, methylethylketone, toluene, ethyl acetate, heptane and the like. Among these solvents, isopropyl alcohol can be particularly advantageously used, because the liquid-absorbing substance can be dissolved therein at a high solubility, along with a high volatility of isopropyl alcohol.

The concentration of the liquid-absorbing substance in the coating solution may be widely varied depending upon the type or degree of the surface activity of the surface active agent used, desired effects and other factors. Generally, the concentration of the liquid-absorbing substance is preferably the amount sufficient to ensure that the stretched film has a liquid absorption capacity, in terms of the amount of water absorbed, of 0.00003 to 0.005 $cm^3$ per unit area. The liquid absorption capacity out of the above scope will not ensure a satisfactory sweat absorption effect in the resulting oil cleaning sheet. Note that the above preferred range of the liquid absorption capacity can be similarly applied to all the oil cleaning sheets of the present invention.

In addition, an aqueous solution of the liquid-absorbing substance distributed on a surface of the stretched film preferably has a surface tension of 15.0 to 36.0 dyn/cm. The surface tension out of the above-described range will not ensure a satisfactory sweat absorption effect in the resulting oil cleaning sheet and also not ensure an effective utilization of the transparency which is provided in the oil cleaning sheet as a result of absorption of sweat and oil cleaning, for evaluating a level of such effects.

In the coating of a coating solution onto the stretched film, the coating operation can be carried out in accordance with the conventional methods. Suitable coating methods include, for example, gravure coating, flexocoating, screen coating, dip coating and spray coating. A coverage of the coating solution on a surface of the stretched film may be widely varied depending upon the type and surface activity of the liquid-absorbing substance used, desired effects and other factors, and generally its satisfactory coverage is in the range of about 0.1 to 3 $g/m^2$.

In the production of the oil cleaning sheet of the present invention, an incorporation method in which the liquid-absorbing substance is incorporated into the stretched film during its production may be used in place of the above-described coating method. For example, in the production of the stretched film, when the starting materials such as the thermoplastic resin, filler, organic nucleating agent and the like are melted and blended, the liquid-absorbing substance may be also blended at any desired timing to produce the desired hydrophilic oil cleaning sheet. In this method, the liquid-absorbing substances described in the above paragraph concerning application of the liquid-absorbing substance by coating may be also used, and the amount of the liquid-absorbing substance to the incorporated is suitably the amount sufficient to ensure the above-described liquid absorption capacity. For this incorporation method, among the many usable liquid-absorbing substances, diethanol amides laurate and the like may be particularly used because of their good resistance to heat and their good hydrophilic property.

EXAMPLES

The present invention will not be explained in further detail by way of examples. In the following examples, the term "parts" refers to "parts by weight" unless otherwise specified. It is also to be understood that the invention is in no way limited to these examples.

Example 1

The following starting material was melt mixed in the amounts listed.

| | |
|---|---|
| Polypropylene resin (available from Union Carbide Co. under trade name "5D45") | 63.3 parts |
| Mineral oil (available from Amoco Oil & Chemical Co. under trade name "White Mineral oil #31") | 34.0 parts |
| Organic nucleating agent (available from Hoechst Celanese under trade name "Blue P-526") | 2.75 parts |

The melt mixture was then cast from an extrusion die onto a cold roll to form a film. The resulting film was subjected to biaxial stretching (180% in lengthwise direction, 180% in widthwise direction). A porous stretched plastic film was obtained having the following characteristics.

| | |
|---|---|
| Film thickness | 0.0035 cm |
| Void content | 25% |
| Interstitial volume per unit area | 0.000875 $cm^3$ |

The resulting porous film was cut into a rectangle of 9 cm length×6 cm width to make a test film which was subjected to quality evaluation with regard to (1) oil absorption, (2) transparency after use and (3) feel of the film, according to the following methods.

(1) Evaluation of Oil Absorption

After measuring the weight (mg) of the test film, it was impregnated with commercially available mineral oil. After standing for one minute, the residual oil on the surface of the film was wiped off with a paper towel and the weight (mg) of the test film was measured again. The change in the weight of the film due to impregnation of the mineral oil was used to determine the amount of absorption per unit area ($mg/cm^2$) and the theoretical absorption (amount of absorption when all of the interstitial of the film are filled with mineral oil, $mg/cm^2$).

(2) Transparency after Use

Test films were used as oil cleaning sheets for makeup in a monitoring test with 20 panelists. After use, the films with very excellent transparency were assigned as excellent (Θ), those with good transparency were assigned as good (O), those with acceptable transparency were assigned as fair (Δ) and those which were stiff with an inferior feel were assigned as poor (x).

The results of each of the evaluation tests were as follows.

| | |
|---|---|
| Film weight (before oil absorption) | 121 mg |
| Film weight (after oil absorption) | 174 mg |
| Change in weight (increase) | 53 mg |
| Oil absorption per unit area | 0.98 mg/cm$^2$ |
| Theoretical absorption | 0.73 mg/cm$^2$ |
| Transparency after use | Excellent (⊖) |
| Feel | Excellent (⊖) |

As these results demonstrate, the porous stretched plastic film of this example was highly suitable as an oil cleaning sheet for makeup. There was also no tearing of the film during the evaluation tests.

Example 2

The method described in Example 1 was repeated. For this example, however, the following starting material was melt mixed in the amounts listed.

| | |
|---|---|
| Polypropylene resin (available from Union Carbide Co. under trade name "SD45") | 62.0 parts |
| Mineral oil (available from Amoco Oil and Chemical Co. under trade name "White Mineral Oil #31") | 35.0 parts |
| Pigment (available from PMS Consolidate Co. under trade name "18P805 Blue Pigment") | 3.0 Parts |
| Organic nucleating agent (available from Milliken Chemical Co. under trade name "Millad 3905") | 0.08 part |

In this example, the porous stretched plastic film was prepared using the inflation method instead of the casting method of Example 1, and a tube shaped film was made by blowing-up the melted moisture from a circular die, which film was then cut into 2 sheet-like films. Each resulting film was then subjected to uniaxial stretching (160% in lengthwise direction).

The characteristics of the resulting porous stretched plastic film and the results of each of the evaluation tests were as follows.

| | |
|---|---|
| Film thickness | 0.0035 cm |
| Void content | 20% |
| Interstitial volume per unit area | 0.0007 cm$^3$ |
| Film weight (before oil absorption) | 172 mg |
| Film weight (after oil absorption) | 211 mg |
| Change in weight (increase) | 39 mg |
| Oil absorption per unit area | 0.72 mg/cm$^2$ |
| Theoretical absorption | 0.59 mg/cm$^2$ |
| Transparency after use | excellent (©) |
| Feel | excellent (®) |

As these results demonstrate, the porous stretched plastic film of this example was highly suitable as an oil cleaning sheet for makeup. There was also no tearing of the film during the evaluation tests.

Example 3

The method described in Example 1 was repeated. For this example, however, the following starting material was melt mixed in the amounts listed.

| | |
|---|---|
| Polypropylene resin (available from Union Carbide Co. under trade name "DX5E98") | 79.0 parts |
| Mineral oil (available from Amoco Oil and Chemical Co. under trade name "White Mineral Oil #31") | 21.0 parts |
| Organic nucleating agent (available from Milliken Chemical Co. under trade name "Millad 3905") | 0.09 parts |

In this example, the porous stretched plastic film was prepared using the inflation method instead of the casting method of Example 1, and a tube-shaped film was made by blowing-up the melted mixture from a circular die, which film was then cut into 2 sheet-like films. Each resulting film was then subjected o uni axial stretching (160% in lengthwise direction).

The characteristics of the resulting porous stretched plastic film and the results of each of the evaluation tests were as follows.

| | |
|---|---|
| Film thickness | 0.0075 cm |
| Void content | 20% |
| Interstitial volume per unit area | 0.0015 cm$^3$ |
| Film weight (before oil absorption) | 281 mg |
| Film weight (after oil absorption) | 338 mg |
| Change in weight (increase) | 57 mg |
| Oil absorption per unit area | 1.06 mg/cm$^2$ |
| Theoretical absorption | 1.26 mg/cm$^2$ |
| Transparency after use | fair (Δ) |
| Feel | good (○) |

As these results demonstrate, the porous stretched plastic film of this example was usable as an oil cleaning sheet for makeup, although its properties were inferior to those of the films of Examples 1 and 2 above. There was also no tearing of the film during the evaluation tests.

Example 4

This example was carried out as a comparative example.

The method described in Example 1 was repeated. For comparison in this example, however, the following starting material was melt mixed in the amounts listed.

Polyethylene resin (available from Fina Oil and Chemical Co. under trade name "Fina 1285") 38.0 parts Mineral oil (available from Witco Co. under trade name "Witco Protol") 62.0 parts In this example, the porous stretched plastic film was prepared using a modified casting method instead of the casting method of Example 1. Specifically, a film was made by casting the milted mixture from an extrusion die onto a cold roll, and then dissolving off the mineral oil with an organic solvent. The resulting film was then subjected to biaxial stretching (240% in lengthwise direction, 280% in widthwise direction).

The characteristics of the resulting porous stretched plastic film and the results of each of the evaluation tests were as follows.

| | |
|---|---|
| Film thickness | 0.005 cm |
| Void content | 75% |
| Interstitial volume per unit area | 0.004 cm$^3$ |
| Film weight (before oil absorption) | 65 mg |
| Film weight (after oil absorption) | 269 mg |
| Change in weight (increase) | 204 mg |

-continued

| | |
|---|---|
| Oil absorption per unit area | 3.78 mg/cm² |
| Theoretical absorption | 3.14 mg/cm² |
| Transparency after use | fair (Δ) |
| Feel | good (○) |

As these results demonstrate, the porous stretched plastic film obtained in this example was usable as an oil cleaning sheet for makeup, although its properties were inferior to those of the films of Examples 1 and 2 above.

Example 5

This example was carried out as a comparative example.

The method described in Example 1 was repeated. For comparison in this example, however, the following starting material was melt mixed in the amounts listed.

| | |
|---|---|
| Polypropylene resin (available from Shell Chemical Co. under trade name "DS SD45") | 30.0 parts |
| Mineral oil (available from Amoco Oil and Chemical Co. under trade name "White Mineral Oil #31") | 70.0 parts |
| Organic nucleating agent (available from Milliken Chemical Co. under trade name "Millad 3905") | 0.08 part |

In this example, the porous stretched plastic film was prepared using a modified casting method instead of the casting method of Example 1. Specifically, a film was made by casting the melted mixture from an extrusion die onto a cold roll, and then dissolving off the mineral oil with an organic solvent. The resulting film was then subjected to biaxial stretching (180% in lengthwise direction, 270% in widthwise direction).

The characteristics of the resulting porous stretched plastic film and the results of each of the evaluation tests were as follows.

| | |
|---|---|
| Film thickness | 0.011 cm |
| Void content | 84% |
| Interstitial volume per unit area | 0.00924 cm³ |
| Film weight (before oil absorption) | 90 mg |
| Film weight (after oil absorption) | 550 mg |
| Change in weight (increase) | 460 mg |
| Oil absorption per unit area | 3.52 mg/cm² |
| Theoretical absorption | 7.74 mg/cm² |
| Transparency after use | poor (X) |
| Feel | good (○) |

As these results demonstrate, the porous stretched plastic film obtained in this example was usable as an oil cleaning sheet for makeup, although assessment of its effect was very difficult and its properties were inferior to those of the film of Examples 1 and 2 above.

Example 6

This example was carried out as a reference example.

For reference, the 3 different oil cleaning sheets for makeup described below (commercially available) were provided for quality evaluation by the methods described in Example 1. The characteristics of the oil cleaning sheets for makeup and the results of each of the evaluation tests were as follows. Oil cleaning sheet for makeup by Y Co. (gold foil embossed sheet)

| | |
|---|---|
| Sheet thickness | 0.0052 cm |
| Void content | — |
| Interstitial volume per unit area | — |
| Film weight (before oil absorption) | 121 mg |
| Film weight (after oil absorption) | 136 mg |
| Change in weight (increase) | 15 mg |
| Oil absorption per unit area | 0.27 mg/cm² |
| Theoretical absorption | — |
| Transparency after use | good (○) |
| Feel | fair (Δ) |

Oil cleaning sheet from makeup by K Co. (natural plant fiber)

| | |
|---|---|
| Sheet thickness | 0.0025 cm |
| Void content | — |
| Interstitial volume per unit area | — |
| Film weight (before oil absorption) | 86 mg |
| Film weight (after oil absorption) | 104 mg |
| Change in weight (increase) | 18 mg |
| Oil absorption per unit area | 0.33 mg/cm² |
| Theoretical absorption | — |
| Transparency after use | good (○) |
| Feel | good (○) |

Oil cleaning sheet for makeup by S. Co. (100% natural pulp, containing natural manila hemp)

| | |
|---|---|
| Sheet thickness | 0.0002 cm |
| Void content | — |
| Interstitial volume per unit area | — |
| Film weight (before oil absorption) | 83 mg |
| Film weight (after oil absorption) | 100 mg |
| Change in weight (increase) | 17 mg |
| Oil absorption per unit area | 0.31 mg/cm² |
| Theoretical absorption | — |
| Transparency after use | good (○) |
| Feel | good (○) |

As these results demonstrate, the oil cleaning sheets for makeup in this example which were tested for reference were usable as oil cleaning sheets for makeup, but their properties were inferior to those of the films of Examples 1 and 2 above.

Example 7

The following starting material was melt mixed in the amounts listed.

| | |
|---|---|
| Polypropylene resin (available from Union Carbide Co. under trade name "SD45") | 36.3 parts |
| Mineral oil (available from Amoco Oil and Chemical Co. under trade name "White Mineral Oil #31") | 34.0 parts |
| Organic nucleating agent (available from Hoechst Celanese under trade name "Blue P-526") | 2.75 part |

The melt mixture was then cast from an extrusion die onto a cold roll to form a film. The resulting film was subjected to biaxial stretching (180% in lengthwise direction, 180% in widthwise direction). A porous stretched plastic film was obtained.

Next, "Leodolsuper L-10(F)", surface active agent commercially available from Kao Co., was dissolved in isopropyl alcohol to prepare a coating solution containing 5% by weight of the surface active agent. The obtained coating solution was coated on a surface of the porous film produced in the above step by using a gravure roll coater (180 lines) and dried. The coated porous film had the following characteristics.

| | |
|---|---|
| Film thickness | 0.0035 cm |
| Void content | 25% |
| Interstitial volume per unit area | 0.000875 cm$^3$ |

The resulting porous film was cut into a rectangle of 9 cm length×6 cm width to make a test film which was subjected to quality evaluation with regard to (1) oil absorption and (2) water absorption, according to the following methods.

(1) Evaluation of Oil Absorption

After measuring the weight (mg) of the test film, it was impregnated with commercially available mineral oil. After standing for one minute, the residual oil on the surface of the film was wiped off with a paper towel and the weight (mg) of the test film was measured again. The change in the weight of the film due to impregnation of the mineral oil was used to determine the amount of oil absorption per unit area (cm$^3$/cm$^2$).

(2) Evaluation of Water Absorption

After measuring the weight (mg) of the test film, it was impregnated with tap water. After standing for one minute, the residual water on the surface of the film was wiped off with a paper towel and the weight (mg) of the test film was measured again. the change in the weight of the film due to impregnation of the tap water was used to determine the amount of water absorption per unit area (cm$^3$/cm$^2$).

The results of the evaluation tests are summarized in the below-described Table 1.

Example 8

The method described in Example 7 was repeated. For this example, however, the following starting material was melt mixed in the amounts listed.

| | |
|---|---|
| Polypropylene resin (available from Union Carbide Co. under trade name "SD45") | 58.0 parts |
| Mineral oil (available from Amoco Oil and Chemical Co. under trade name "White Mineral Oil #31") | 35.0 parts |
| Organic nucleating agent (available from Hoechst Celanese under trade name "Blue P-526") | 5.0 parts |
| Surface active agent (available from Hoechst Celanese under trade name "Hostastat System E5952" | 2.0 parts |

The results of the evaluation tests are summarized in the following Table 1.

| | Example 7 | Example 8 | Reference Example |
|---|---|---|---|
| Film thickness | 35 μm | 35 μm | 25 μm |
| Void content | 25% | 20% | — |
| Interstitial volume per unit area | 0.000875 cm$^3$ | 0.0007 cm$^3$ | — |
| Oil absorption per unit area (cm$^3$/cm$^2$) | 0.00106 | 0.0096 | 0.00032 |
| Water absorption per unit area (cm$^3$/cm$^2$) | 0.00092 | 0.00078 | 0.00038 |

In the above Table 1, the "Reference Example" shows the results obtained when the oil cleaning sheet (gold foil-embossed sheet) produced by Y Co. was subjected to the evaluation tests in accordance with the manner described in Example 7. As will be understood from the results of Table 1, the oil cleaning sheet according to the present invention having a hydrophilic surface can exhibit excellent functions in both of the oil absorption and the water absorption (sweat absorption), in comparison with the prior art oil cleaning sheet.

Example 9

The method described in Example 7 was repeated. For this example, however, to study any influence of the surface active agent on the oil absorption and water absorption (sweat absorption), different surface active agents which chemical name and trade name are described in the below-mentioned Table 2 were used in the same amount as in Example 7 to prepare oil cleaning sheets. Further, the commercially available microporous film (untreated) and the commercially available oil cleaning sheet (gold-foil-embossed sheet) produced by Y Co. were also used for the comparison purpose. Note that the HLB value (hydrophilic-lipophilic balance) of each surface active agent and a surface tension (dyn/cm) of each coating solution having dissolved therein the surface active agent are also described in Table 2.

As a result of the evaluation tests made in accordance with the manner described in Example 7, the results summarized in the following Table 2 were obtained. In Table 2, the oil absorption means an amount of the oil absorption per unit area (cm$^3$/cm$^2$) and the water absorption means an amount of the water absorption per unit area (cm3/cm2). Further, after oil absorption and after water absorption, each oil cleaning sheet was visually inspected with regard to change in color, and the color change was classified under "excellent" (excellent change), "good" (good change) and "bad" (poor change). The results are summarized in the following Table 2.

| Surface active agent | | | | | Change in color | | Surface tension |
| --- | --- | --- | --- | --- | --- | --- | --- |
| Chemical name | Trade name | HLB | Oil absorption | Water Absorption | after oil absorption | after water absorption | (dyn/cm) |
| Sorbitan monooleat | Leodol SP-010 | 4.3 | 0.00115 | 0.00080 | excellent | bad | 29.6* |
| Sorbitan monostearate | Leodol super SP-S10 | 4.7 | 0.00106 | 0.00002 | excellent | bad | 37.1 |
| Sorbitan monostearate | Leodol super SP-L10 | 8.6 | 0.00122 | 0.00092 | excellent | excellent | 29.1 |
| Polyoxyethylene laurylether | Emulgen 105 | 9.7 | 0.00113 | 0.00085 | excellent | excellent | 26.8 |
| Polyoxyethylene laurylether | Emulgen 109P | 13.6 | 0.00088 | 0.00085 | excellent | excellent | 31.8 |
| Polyoxymethylene sorbitan monolaurate | Leodol super TW-L12 | 16.7 | 0.00112 | 0.00094 | excellent | excellent | 35.8 |
| Polyoxyethylene octoylphenylether | Emulgen 840S | 17.9 | 0.00111 | 0.00018 | excellent | bad | 46.0 |
| Polyethyleneglycol distearate | Ememon 3299R | 19.2 | 0.00125 | 0.00000 | excellent | bad | 48.9 |
| Ammonium laurylsulfate | Emul AD-25R | — | 0.00110 | 0.00080 | excellent | excellent | 32.3 |
| Sodium dodecylbenzene sulfonate | Neopelex F-25 | — | 0.00120 | 0.00088 | excellent | excellent | 35.9 |
| Lauryl betaine | Anhitol 24B | — | 0.00113 | 0.00074 | excellent | excellent | 31.5 |
| Microporous Film (untreated) | | — | 0.00116 | 0.00000 | excellent | bad | — |
| Oil cleaning sheet by Y Co. | | — | 0.00032 | 0.00038 | good | good | — |

The evaluation results described in Table 2 indicate that the excellent oil absorption and water absorption (sweat absorption) desired for the present invention cannot be obtained if the used surface active agent is out of the range of the present invention, and that such results can be varied principally depending on the surface tension of the surface active agent used. Referring to the data of the surface active agent used. Referring to the data of the surface tension in Table 2, it is apparent that the surface tension of the aqueous solution of the surface active agent is desirably 36 dyn/cm or less to obtain the desired oil absorption and water absorption (sweat absorption).

As explained above, according to the present invention an oil cleaning sheet for makeup is constructed not of conventional fiber material paper but is formed of a porous film made of a plastic material, with fine voids provided in the film to cause adsorption of oils which have surfaced on the face; it is therefore possible to realize high absorption of oils, to clearly assess the absorbing effect based on the excellent transparency of the oil absorbing areas and to thus provide the user with a feeling of adequate wiping and a sense of satisfaction, while the sheet has an agreeable feel, is resistant to damage during use, and requires no inclusion of particulate bodies on the surface for improved characteristics.

Further, according to the present invention, since a hydrophilic property was applied to a surface of the porous film of the plastic material, remarkable effects that a large amount of the sweat and skin oil dissolved therein on the face an be absorbed in the oil cleaning sheet, in addition to the above effects such as excellent absorption o the skin oil, notable transparency indicative of easy confirmation of oil absorption, and toughness. The sweat absorption effect is particularly important in the summer season in which remarkable sweating is unavoidable. Using the oil cleaning sheet of the present invention, undesirable adhesion of the sheet to the skin can be effectively prevented, thereby eliminating an uncomfortable feeling, in addition to complete removal of the sweat from the face. Furthermore, since the surface active agent can additionally act as an antistatic agent, the used oil cleaning sheet can be discarded without disadvantage concerning its adhesion to the hand.

What is claimed is:

1. A method of removing facial oil comprising providing an oil cleaning sheet comprising a porous stretched film made of a crystalline thermoplastic resin, the porous film containing voids where the voids contain a filler selected from mineral oils, glycerin, petroleum jelly, low molecular weight polyethylene, polyethylene oxide, polypropylene oxide, polytetramethylene oxide and mixtures thereof wherein the size of the voids is in the range of 0.2 to 5 µm wiping a user's skin to remove skin oil wherein the oil cleaning sheet is capable of becoming more transparent upon absorption of a given amount of facial oil per unit area.

2. The method of claim 1 wherein the interstitial volume per unit area of said porous stretched film is in the range of 0.0001–0.005 cm$^3$ as calculated by the following equation:

interstitial volume per unit area=[film thickness (cm)×1 (cm)×void content (%)]/100 (where the void content is the percentage of voids in the porous film).

3. The method of claim 1 wherein the void content of said porous stretched film is in the range of 5–50% and the film thickness is in the range of 5–200 µm.

4. The method of claim 1 wherein at least one surface of said porous stretched film contains a hydrophilic liquid-absorbing substance which is at least partly distributed on the surface.

5. The method of claim 4 wherein said liquid-absorbing substance is distributed on the surface of said stretched film by coating the same, after said stretched film was produced.

6. The method of claim 4 wherein said liquid-absorbing substance is incorporated into said stretched film during production thereof so that said substance is at least partly exposed in a surface of said film.

7. The method of claim 4 herein said porous stretched film has a liquid absorption capacity, in terms of the amount of water absorbed, of 0.00003 to 0.005 cm$^3$ per unit area.

8. The method of claim 4 wherein an aqueous solution of said liquid-absorbing substance has a surface tension of 15.0 to 36.0 dyn/cm.

* * * * *

UNITED STATES PATENT AND TRADEMARK OFFICE
CERTIFICATE OF CORRECTION

PATENT NO. : 7,157,093 B1
APPLICATION NO. : 09/582838
DATED : January 2, 2007
INVENTOR(S) : Kazunori Kondoh It is certified that error appears in the above-identified patent and that said Letters Patent is hereby corrected as shown below:

Col. 2, Line 63: Delete "desireable" and insert -- desirable --, therefor.

Col. 5, Line 3: Delete "antitstatic" and insert -- antistatic --, therefor.

Col. 6, Line 42: Delete "insorfar" and insert -- insofar --, therefor.

Col. 6, Line 51: Delete "suface" and insert -- surface --, therefor.

Col. 10, Line 7: Delete "0.09 parts" and insert -- 0.09 part --, therefor.

Col. 10, Line 15: After "subjected" delete "o" and insert -- to --, therefor.

Col. 10, Line 15: Delete "uni axial" and insert -- uniaxial --, therefor.

Col. 10, Line 45: After "38.0 parts" insert -- . --.

Col. 10, Line 47: After "62.0 parts" insert -- . --.

Col. 11, Line 67: After "sheet)" insert -- . --.

Col. 12, Line 18: After "fiber)" insert -- . --.

Col. 12, Line 34: After "hemp)" insert -- . --.

Col. 12, Line 64: Delete "2.75 part" and insert -- 2.75 parts --, therefor.

Col. 13, Line 46: After "again." delete "the" and insert -- The --, therefor.

Col. 14, Line 61: Delete "(cm3/cm2)," and insert -- ($cm^3/cm^2$). --, therefor.

Col. 15, Line 13: Delete "octoylphenylether" and insert -- octylphenylether --, therefor.

Col. 17, Line 6: In Claim 6, after "thereof" insert -- , --.

UNITED STATES PATENT AND TRADEMARK OFFICE
CERTIFICATE OF CORRECTION

PATENT NO. : 7,157,093 B1
APPLICATION NO. : 09/582838
DATED : January 2, 2007
INVENTOR(S) : Kazunori Kondoh It is certified that error appears in the above-identified patent and that said Letters Patent is hereby corrected as shown below:

Col. 18, Line 1: In Claim 7, delete "herein" and insert -- wherein --, therefor.

Signed and Sealed this

Twenty-second Day of May, 2007

JON W. DUDAS
*Director of the United States Patent and Trademark Office*